US008865874B2

(12) United States Patent
Kirihata et al.

(10) Patent No.: US 8,865,874 B2
(45) Date of Patent: Oct. 21, 2014

(54) HAPTEN COMPOUND AND ANTIBODY

(75) Inventors: Mitsunori Kirihata, Osaka (JP); Tomoyuki Asano, Osaka (JP); Kohki Uehara, Osaka (JP)

(73) Assignees: Japan Science and Technology Agency, Osaka (JP); Osaka Prefecture University, Osaka (JP); Stella Chemifa Corporation, Osaka (JP)

( * ) Notice: Subject to any disclaimer, the term of this patent is extended or adjusted under 35 U.S.C. 154(b) by 1568 days.

(21) Appl. No.: 12/280,538

(22) PCT Filed: Oct. 5, 2006

(86) PCT No.: PCT/JP2006/319977
§ 371 (c)(1),
(2), (4) Date: Sep. 9, 2009

(87) PCT Pub. No.: WO2007/097065
PCT Pub. Date: Aug. 30, 2007

(65) Prior Publication Data
US 2009/0317920 A1    Dec. 24, 2009

(30) Foreign Application Priority Data
Feb. 23, 2006  (JP) ................................. 2006-046950

(51) Int. Cl.
| C07K 16/00 | (2006.01) |
| C12P 21/08 | (2006.01) |
| C07K 16/44 | (2006.01) |
| G01N 33/53 | (2006.01) |
| G01N 33/94 | (2006.01) |
| C07F 5/02 | (2006.01) |
| G01N 33/84 | (2006.01) |

(52) U.S. Cl.
CPC ............ G01N 33/5308 (2013.01); C07K 16/44 (2013.01); G01N 33/94 (2013.01); C07F 5/027 (2013.01); G01N 33/84 (2013.01)
USPC ..................... 530/388.9; 530/388.1; 436/548; 435/70.21

(58) Field of Classification Search
CPC ....... C07K 16/44; G01N 33/94; G01N 33/84; G01N 33/5308
See application file for complete search history.

(56) References Cited

U.S. PATENT DOCUMENTS

| 4,533,493 A | 8/1985 | Benovic et al. |
| 6,228,362 B1 | 5/2001 | Griffiths et al. ............ 424/175.1 |
| 7,115,718 B2 | 10/2006 | McConnell et al. |

FOREIGN PATENT DOCUMENTS

| EP | 1 988 094 | 11/2008 |
| JP | 2207086 | 8/1990 |
| JP | 7330773 | 12/1995 |
| JP | 2001233883 | 8/2001 |

OTHER PUBLICATIONS

Otersen et al. Binding and distribution of Na2B12H11SH on cellular and subcellular level in tumor tissue of glioma patients in boron neutron capture therapy. Journal of Neuro-Oncology 1997, vol. 33, pp. 131-139.*
Ranadive et al. A technique to prepare boronated B72.3 monoclonal antibody for boron neutron capture therapy. Nuclear Medicine and Biology,1993 vol. 20, Issue 1, pp. 1-6. Abstract attached, pp. 1-3.*
Gilbert et al. Spectromicroscopy of boron in human glioblastomas following administration of Na2B12H11SH. Physical Review E 2000, vol. 62, No. 1, pp. 1110-1118.*
Chappey et al. Monoclonal antibodies in hapten Immunoassays. Pharmaceutical Research 1992, vol. 9, No. 11, pp. 1375-1379.*
Rudikoff et al. Single amino acid substitution altering antigen-binding specificity. Proc. Natl. Acad. Sci. 1982, vol. 79. pp. 1979-1983.*
Office Action issued in Chinese Application No. 200680053176.7, issued Jan. 18, 2011 (and English language translation thereof).
Office Action issued in European Application No. 06 811 315.8, issued Sep. 29, 2011.
Australian Patent Office, Action against corresponding Australian Patent Application No. 2006338844; pp. 1-2; issued Mar. 25, 2010; published in AU.
Extended European Search Report issued in European Application No. 06811315.8, mailed Sep. 27, 2010.
Maruyama et al., "Intracellular targeting of sodium mercaptoundecahydrododecaborate (BSH) to solid tumors by transferring-PEG liposomes, for boron neutron-capture therapy (BNCT)," *Journal of Controlled Release*, 98:195-207, 2004.
Korean Intellectual Property Office Notice of Preliminary Rejection (Translation) issued Dec. 28, 2009 during the prosecution of Korean Patent Application No. 10-2008-7023154.
Allen et al., "Progress in neutron capture therapy for cancer," Conference Book, Conference: 4. International Symposium on Neutron Capture Therapy for Cancer, Sydney (Australia). Plenum Press, New York, NY (US) Pub. Sep. 1, 1992 pp. 223-226.

(Continued)

Primary Examiner — Shafiqul Haq
(74) Attorney, Agent, or Firm — Fulbright & Jaworski LLP

(57) ABSTRACT

The present invention is a compound having a structure represented by the following formula (1):

[Chemical formula 1]

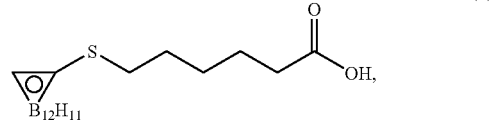

(1)

and an antibody to BSH obtained by using the compound as a hapten and using a complex of the hapten and a high-molecular compound as an antigen. By using the present invention, it becomes possible to provide a hapten compound for preparing an antibody recognizing BSH highly sensitively and highly selectively, an antibody to BSH, as well as a kit for measuring BSH and an immunological measuring method having high sensitivity and excellent in quantitative property using the antibody.

4 Claims, 1 Drawing Sheet

(56) References Cited

OTHER PUBLICATIONS

Al-Madhoun et al., "Synthesis of a Small Library of 3-(Carboranylalkyl)thymidines and Their Biological Evaluation as Substrates for Human Thymidine Kinases 1 and 2," J. Med. Chem. 2002 vol. 45 pp. 4018-4028.

Cai et al, "Boron-Containing Polyamines as DNA Targeting Agents for Neutron Capture Therapy of Brain Tumors: Synthesis and Biological Evaluation," J. Med. Chem. 1997 vol. 40 3887-3896.

Compostella et al., "Synthesis of Glycosyl Carboranes with Different Linkers Between the Sugar and the Boron Cage Moieties," Monduzzi Editore S. p. A.—Medimond Inc. Essen, Germany, Sep. 2002, pp. 81-84.

International Preliminary Report on Patentability issued Aug. 28, 2008, during the prosecution of International Application No. PCT/JP2006/319977. Published Aug. 26, 2008.

Imamura et al., "Synthesis and in Vitro Evaluation of 5-closo- and 5-nido-Orthocarboranyluridines as Boron Carriers," Bulletin of the Chemical Society of Japan 1997, vol. 70(12) pp. 3103-3110.

International Search Report issued Dec. 19, 2006, during the prosecution of Japanese Patent Application No. PCT/JP2006/319977. Published Aug. 30, 2007.

Kageji et al., "Subcellular biodistribution of sodium borocaptate (BSH: Na2B12H11SH) in a rat glioma model in boron neutron capture therapy," J Neurooncol. Sep. 2002, vol. 59(2):135-42.

Kultyshev et al., "S-alkylation and S-amination of methyl thioethers—derivatives of closo-[B(12)H(12)](2-). synthesis of a boronated phosphonate, gem-bisphosphonates, and dodecaborane-ortho-carborane oligomers," Journal of the American Chemical Society 2002;124(11):2614-24.

Lim et al., "o-Carboranyl derivatives of 1,3,5-s-triazines," Monduzzi Editore S. p. A.—Medimond Inc. Essen, Germany, Sep. 2002, pp. 37-4142.

Nagasawa et al., "Synthesis of Polyhedral borane derivatives having a carboxy group," Tetrahedron Letters 1990. vol. 31(28) pp. 4029-4032.

Office Action issued during the prosecution of corresponding Japanese Patent Application No. 2007-511118.

Okuyama et al., "Development of monoclonal antibodies against coplaner polychlorinated biphenyls," Dec. 15, 2000 p. 141, PA-21. Academic Society Home Village Scientific Program Weblink: http://wwwsoc.nii.ac.jp/jsedr/sympo/3symposium/english/posterprogrameng.htm.

Otersen et al., "Binding and distribution of Na2B12H11SH on cellular and subcellular level in tumor tissue of glioma patients in boron neutron capture therapy," Journal of Neuro-Oncology, May 1997 vol. 33( 1-2) pp. 131-139.

Slepukhina et al.., "Fragmentation of B12 H11 S-R(2-) in electrospray mass spectrometry," Journal of Organometallic Chemistry 2005, vol. 690 (11), pp. 2796-2801.

Tjarks, "The use of boron clusters in the rational design of boronated nucleosides for neutron capture therapy of cancer," Journal of Organometallic Chemistry vols. 614-615, Dec. 8, 2000, pp. 37-47.

Written Opinion issued Aug. 28, 2008, during the prosecution of International Application No. PCT/JP2006/319977. Published Aug. 23, 2008.

Wyzlic et al., "A general, convenient way to carborane-containing amino acids for boron neutron capture therapy," Tetrahedron letters 1992, vol. 33(49), pp. 7489-7490.

Harris, Lisa J., et. al.; "Crystallization of Intact Monoclonal Antibodies"; Proteins: Structure, Function, and Genetics 23:285-289 (1995).

Parkkinen, Tarja, et. al.; "Crystal Structures of an Enantioselective Fab-fragment in Free and Complex Forms"; J. Mol. Biol. (2006); 357:471-480.

Pozharski, Edwin, et. al.; "Diversity in Hapten Recognition: Structural Study of an Anti-cocaine Antibody M82G2"; J. Mol. Biol. (2005); 349:570-582.

Almagro, Juan C.; "Identification of Differences in the Specificity-Determining Residues of Antibodies that Recognize Antigens of Different Size: Implications for the Rational Design of Antibody Repertoires"; Journal of Molecular Recognition 2004; 17:132-143.

M-P Lefranc; "IMGT® Databases, Web Resources and Tools for Immunoglobulin and T cell Receptor Sequence Analysis, http://imgt.cines.fr"; Luekemia (2003); 17:260-266.

Lefranc, Marie-Paule; "Review—IMGT-Ontology and IMGT Databases, Tools and Web Resources for Immunogenetics and Immunoinformatics"; Molecular Immunology (2004); 40:647-660.

Möller; Heiko, et. al.; "NMR-Based Determination of the Binding Epitope and Conformational Analysis of MUC-1 Glycopeptides and Peptides Bound to the Breast Cancer- Selective Monoclonal Antibody SM3"; Eur. J. Biochem. (2002); 269:1444-1455.

Berman, Helen M., et. al.; "The Protein Data Bank"; Nucleic Acids Research (2000); vol. 28, No. 1; pp. 235-242.

Chinese Office Action, issued Dec. 17, 2012 (published Dec. 17, 2012) during the prosecution of Chinese Application No. 200680053176.7.

Chinese Office Action Issued Mar. 28, 2012 during prosecution of corresponding Chinese Application No. 200680053176.7.

* cited by examiner

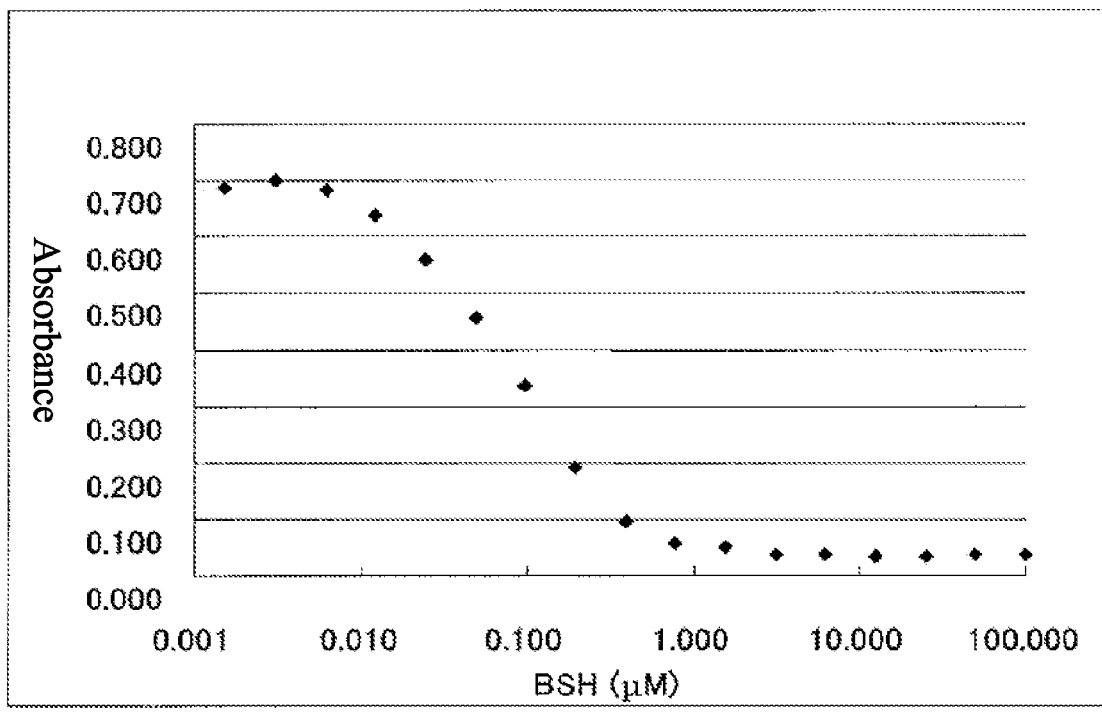

HAPTEN COMPOUND AND ANTIBODY

This Application is a National Phase Application of International Application No. PCT/JP2006/319977 filed Oct. 5, 2006, which claims priority to Patent Application in JP No. 2006-046950, filed Feb. 23, 2006.

TECHNICAL FIELD

The present invention relates to such as a hapten compound of mercaptoundecahydrododecaborate (BSH), an antibody against BSH and an immunological measurement method using the same and is useful particularly for detection and quantification of a neutron capture therapeutic agent used in boron-neutron capture therapy (BNCT).

BACKGROUND ART

In recent years, boron-neutron capture therapy (BNCT) attracts attention as a new therapeutic method for cancer by utilizing a radioisotope. In boron-neutron capture therapy, a boron compound containing a $^{10}$boron isotope ($^{10}$B) is incorporated into a cancer cell, which is then irradiated with a low-energy neutron ray (for example, thermal neutron) to destruct the cancer cell locally by a nuclear reaction occurring in the cell. In this therapeutic method, the selective accumulation of a $^{10}$B-containing boron compound in cells of cancer tissue is critical in enhancing the therapeutic effect, thus it is necessary to develop boron compounds that is incorporated selectively into cancer cells.

Conventionally, boron-containing compounds having a boron atom or a boron atomic group introduced into their basic skeleton have been synthesized as drugs used in BNCT. Clinically used drugs include p-boronophenylalanine (BPA) and mercaptoundecahydrododecaborate (BSH). Among these drugs, BSH is used mainly in treatment of a brain tumor in the form of a sodium salt and confirmed to be useful (see, for example, Non-Patent Documents 1 to 8).

Non-Patent Document 1: I. M. Wyzlic et al., Tetrahedron Lett., 1992, 33, 7489-7490.
Non-Patent Document 2: W. Tjark, J. Organomet. Chem., 2000, 614-615, 37-47.
Non-Patent Document 3: K. Imamura et al., Bull. Chem. Soc. Jpn., 1997, 70, 3103-3110.
Non-Patent Document 4: A. S. Al-Madhorn et al., J. Med. Chem., 2002, 45, 4018-4028.
Non-Patent Document 5: F. Compostella et al., Res. Develop. Neutron Capture Ther., 2002, 81-84.
Non-Patent Document 6: S. B. Kahl et al., Progress in Neutron Capture Therapy for Cancer, Plenum Press, New York 1992, 223.
Non-Patent Document 7: J. Cai et al., J. Med. Chem., 1997, 40, 3887-3896.
Non-Patent Document 8: H. Lim et al., Res. Develop. Neutron Capture Ther., 2002, 37-42.

DISCLOSURE OF THE INVENTION

Problems to be Solved by the Invention

However, the in vivo behavior of BSH involved in BNCT, particularly the microscopic distribution of BSH in a cell surface or in a cell, is still not revealed, and there is a strong demand for a method capable of easily and rapidly measuring the in vivo behavior of BSH qualitatively or quantitatively. An immunological measurement method is expected to be an excellent method for detection or quantification of BSH, but a small-molecular inorganic compound such as BSH is poor in antigenicity for reasons such as its low molecular weight and volume and easy ionization, therefore an antibody capable of detecting BSH highly sensitively has not been obtained until now.

Accordingly, an objective of the present invention is to provide a hapten compound for production of an antibody recognizing BSH highly sensitively and highly selectively, an antibody against BSH, as well as a kit for measuring BSH and a method for immunological measurement of BSH, which are made highly sensitive and excellent in quantification by using the antibody.

Means for Solving the Problems

Focusing attention on a hapten compound having a linker bound to an SH group in a side chain of BSH, the present inventors made extensive study to achieve the objective described above, and as a result, they found that the hapten compound, antibody, hybridoma etc. shown below can achieve the objective, and the present invention was thereby completed.

That is, the present invention relates to a compound having a structure represented by the following formula (1):

[Chemical formula 1]

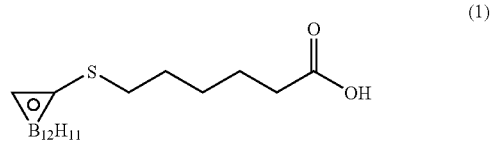

(1)

The present invention relates to an antibody against mercaptoundecahydrododecaborate (BSH), which is obtained by using a conjugate of the above compound as a hapten and a high-molecular compound. The above antibody is preferably a monoclonal antibody.

The present invention relates to a hybridoma producing the above monoclonal antibody. The above hybridoma is preferably Hybridoma BSF-2 (Accession No. ABP-10689).

The present invention relates to a kit for measuring mercaptoundecahydrododecaborate (BSH), which includes the above monoclonal antibody.

The present invention also relates to a method for measuring mercaptoundecahydrododecaborate (BSH), which includes using the above monoclonal antibody or the above kit.

Effect of the Invention

The compound of the present invention is used preferably as a BSH hapten. A conjugate of the hapten and a high-molecular compound can be used to satisfactorily induce an immune response to BSH in an animal, to give a specific and highly sensitive BSH antibody.

The antibody of the present invention can specifically and highly sensitively detect BSH. When the antibody is a monoclonal antibody, it is particularly highly sensitive to BSH and is low in crossreactivity. The hybridoma of the present invention can produce the above monoclonal antibody stably in a short period of time, and the hybridoma can be cultured to produce a large amount of the monoclonal antibody.

The kit of the present invention contains the monoclonal antibody of the present invention, thereby making it preferably useful in a method for immunological measurement of BSH, and can provide a means capable of measuring BSH specifically, highly sensitively and easily.

The method for measuring BSH according to the present invention can exhibit an effect of being excellent in sensitivity, specificity and operational convenience by using the monoclonal antibody or kit of the present invention.

BRIEF DESCRIPTION OF THE DRAWING

FIG. 1 is a graph showing a relationship between BSH concentration and absorbance in direct competitive ELISA using the monoclonal antibody of the present invention.

BEST MODE FOR CARRYING OUT THE INVENTION

The present invention provides a compound having a structure represented by the following formula (1):

[Chemical formula 2]

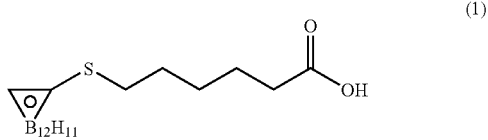

(1)

The above compound is 6-S-undecahydrododecaborylhexanoic acid and is used preferably as a BSH hapten. In the above formula (1), the carboxyl group is bound covalently to a high-molecular compound described later, to form a conjugate (complex).

Production of the above BSH hapten can be carried out by a known synthesis method and is not particularly limited. For example, the method shown in the following reaction scheme is preferably used because the compound can be obtained in high yield in each step.

[Chemical formula 3]

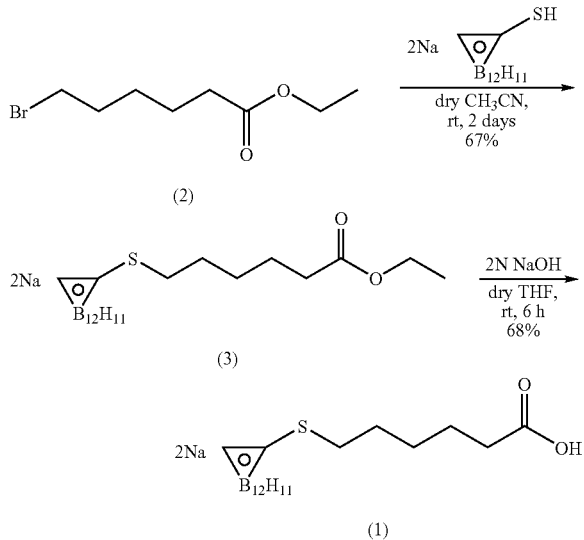

In the above reaction scheme, any starting compounds such as the compound of formula (2) and BSH are easily available compounds.

The synthesis method in the above each step will be described in detail in Example 1.

The above mercaptoundecahydrododecaborate (BSH) has an icosahedral boron cluster structure composed of boron, hydrogen and sulfur atoms. Although BSH is an inorganic low-molecular compound, BSH has a volume larger than that of a benzene ring, has so-called a three center bond structure wherein 3 boron atoms have 2 electrons in common, and is in a unique structure wherein electrons are localized. In the present invention, BSH is represented by the following formula (4) or (5):

[Chemical formula 4]

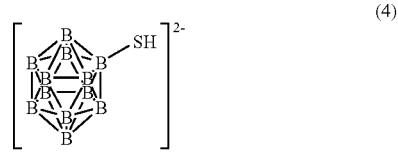

(4)

[Chemical formula 5]

(5)

The above BSH hapten is conjugated with a high-molecular compound (protein) such as bovine serum albumin (BSA), rabbit serum albumin (RSA), ovoalbumin (OVA), keyhole limpet hemocyanine (KLH), thyroglobulin (TG) and immunoglobulin and then used as immunogen.

The method of forming the conjugate may be a known method and is not particularly limited. For example, a carboxy group of the BSH hapten can be reacted with a functional group (for example, an amino group or the like) of the above high-molecular compound by a mixed acid anhydride method, an active ester method or the like to form the conjugate.

The present invention provides an antibody against BSH, which is obtained by using, as an antigen, a conjugate of the above hapten and a high-molecular compound.

The "antibody" referred to in the present invention includes a polyclonal antibody and a monoclonal antibody and also includes a part of an antibody having antigen-binding property such as a Fab fragment and a F(ab')$_2$ fragment. Among these antibodies, a monoclonal antibody is preferable.

A method of producing the above antibody is known, and the antibody of the present invention can also be produced according to a conventional method (Current Protocol in Molecular Biology, Chapter 11.12-11.13 (2000)). Specifically, when the antibody of the present invention is a polyclonal antibody, a conjugate of the above BSH hapten and a high-molecular compound is formed according to a conventional method, and then a nonhuman animal such as a rabbit is immunized with the conjugate, and from serum of the immunized animal, the polyclonal antibody of the present invention can be obtained according to a conventional method.

On the other hand, when the antibody of the present invention is a monoclonal antibody, a nonhuman animal such as a mouse is immunized with the above conjugate by a conventional method, and then the resulting spleen cell is subjected to cell fusion with a myeloma cell to prepare a hybridoma cell which is then screened, and the resulting monoclonal antibody-producing hybridoma can be cultured to give the monoclonal antibody of the present invention (Current Protocols in Molecular Biology edit. Ausubel et al. (1987) Publish. John Wiley and Sons, Sections 11.4-11.11).

Preparation of the antibody can be carried out by a suitable combination of concentration and purification methods such as ultrafiltration, ammonium sulfate fractionation, ion-exchange chromatography, gel filtration chromatography and affinity chromatography.

Specifically, the above antibody can include, for example, an antibody having the following nucleotide sequences of heavy and light chains of a monoclonal antibody obtained in the Examples of the present invention or an antibody having the following amino acid sequences of heavy and light chains of a monoclonal antibody obtained in the Examples of the present invention. As long as the above nucleotide sequences or amino acid sequences exhibit the effect of the present invention, the sequences also include those that have a sequence in which a part of the above sequence is deleted, added, modified, substituted, or mutated. In this case, the homology between the above sequences and those that have a sequence in which a part of the above sequence is deleted, added, modified, substituted, or mutated is preferably 70% or more, more preferably 80% or more, still more preferably 90% or more and further more preferably 95% or more.

[Chemical formula 6]
(5'-)CTCGAGTCTGGCCCTGGAATATTGCAGCGCTCCCAGA

CCCTCAGTCTGACTTGTTCTTTCTCTGGGTTTTCACTGAGCA

CTTCTGGTATGGGTGTTGGCTGGTTTCGTCAGCCTTCAACAA

AGGGTCTAGAGTGGCTGGCAGACATTTGGTGGAATGACAATA

AATACTATAATCCATCCCTGAAGAGCCGGCTCACAATCTCCA

AGGATACCTCCAAAAACCAGGTATTCCTCAAGATCGCCAGTG

TGGACACTATAGATACTGCCACTTACTACTGTTCTCTAAGAA

ATAGTGCCGAAAAGACAAACACCTGGGGCCAAGGCACCACTC

TCACAGTCTCCTCAGCCAAAACGACACCCCATCTGTCTATC

CACTGGCCCCTGGATCTGCTGCCCAAACTAACTCCATGGTGA

CCCTGGGATGCCTGGTCAAGGGCTATTTCCCTGAGCCAGTGA

CAGTGACCTGGAACTCTGGATCCCTGTCCAGCGGTGTGCACA

CCTTCCCAGCTGTCCTGCAGTCTGACCTCTACACTCTGAGCA

GCTCAGTGACTGTCCCCTCCAGCACCTGGCCCAGCGAGACCG

TCACCTGCAACGTTGCCCACCCGGCCAGCAGCACCAAGGTGG

ACAAGAAAATTGTGCCCAGGGATTGTACTAGT

[Chemical formula 7]
(5'-)GAGCTCGTTGTGACTCAGGAATCTGCACTCACCACA

TCACCTGGTGAAACAGTCACACTCACTTGTCGCTCAAGTACT

GGGGCTGTTACAACTAGTAACTATGTCAATTGGGTCCAAGAA

AAACCAGATCATTTATTCACTGGTCTAATAGGTGGTACCAAC

AACCGAGCTCCAGGTGTTCCTGCCAGATTCTCAGGCTCCCTG

ATTGGAGACAAGGCTGCCCTCACCATCACAGGGGCACAGACT

GAGGATGAGGCAATATATTTCTGTGGTCTATGGTACAGCAAC

CATTGGGTGTTCGGTGGAGGAACCAAACTGACTGTCCTAGGC

CAGCCCAAGTCTTCGCCATCAGTCACCCTGTTTCCACCTTCC

TCTGAAGAGCTCGAGACTAACAAGGCCACACTGGTGTGTACG

ATCACTGATTTCTACCCAGGTGTGGTGACAGTGGACTGGAAG

GTAGATGGTACCCCTGTCACTCAGGGTATGGAGACAACCCAG

CCTTCCAAACAGAGCAACAACAAGTACATGGCTAGCAGCTAC

CTGACCCTGACAGCAAGAGCATGGGAAAGGCATAGCAGTTAC

AGCTGCCAGGTCACTCATGAAGGTCACACTGTGGAGAAGAGT

TTGTCCCGTGCTGAGTGTTCCTAATTCTAGA

[Chemical formula 8]
(N-)LESGPGILQRSQTLSLTCSFSGFSLSTSGMGVGWFRQP

STKGLEWLADIWWNDNKYYNPSLKSRLTISKDTSKNQVFLKI

ASVDTIDTATYYCSLRNSAEKTNTWGQGTTLTVSSAKTTPPS

VYPLAPGSAAQTNSMVTLGCLVKGYFPEPVTVTWNSGSLSSG

VHTFPAVLQSDLYTLSSSVTVPSSTWPSETVTCNVAHPASST

KVDKKIVPRDCTS

[Chemical formula 9]
(N-)ELVVTQESALTTSPGETVTLTCRSSTGAVTTSNYVNWV

QEKPDHLFTGLIGGTNNRAPGVPARFSGSLIGDKAALTITGA

QTEDEAIYFCGLWYSNHWVFGGGTKLTVLGQPKSSPSVTLFP

PSSEELETNKATLVCTITDFYPGVVTVDWKVDGTPVTQGMET

TQPSKQSNNKYMASSYLTLTARAWERHSSYSCQVTHEGHTVE

KSLSRAECS

The present invention also provides a hybridoma producing the above-mentioned monoclonal antibody. Hereinafter, a method of preparing the hybridoma in mice is described in detail.

Hereinafter, the method is described by reference to in Balb/c mice. The antigen (immunogen) prepared as described above is dissolved in a physiological phosphate buffer to be a concentration of about 2 mg/ml, and the resulting solution is mixed with an equal volume of an adjuvant and then administered intraperitoneally to Balb/c mice. Thereafter, booster immunization is conducted every about 2 weeks.

From the above mouse with an increased antibody titer in serum from blood collected from a tail blood vessel, the spleen is excised and placed in a DMEM medium (Dulbecco's modified Eagle medium) in a petri dish, and cells are removed from the spleen. The medium is transferred to a centrifuge tube, then large tissue fragments are sedimented, a supernatant in which spleen cells are floating is gently taken, and the single-cell suspension is centrifuged at a low speed to collect the cells. In this manner, the spleen cells are prepared.

A myeloma cell (P3x63Ag8.653) of a mouse is mixed at a ratio of the number of cells of 5:1 (myeloma cell:spleen cell), and this is centrifuged at a low speed to collect cells. Precipitated cells are loosened, and 1 ml of a 50% polyethylene glycol (molecular weight 1,500) solution warmed at 37° C. is slowly added to perform cell fusion.

After cell fusion, 9 ml of a DMEM medium is added, and 40 ml of a bovine fetal serum-containing DMEM medium is further added. To cells collected by centrifugation is added a HAT medium to the number of cells of $5 \times 10^5$/ml to suspend, a cell suspension is dispensed into a 96-well plastic plate at an amount of 250 μl/well, and this is cultured in an incubator under condition of 37° C., 5% carbonic acid gas and warming.

After one week, a half amount of the medium in a well is replaced with a HAT medium, followed by culturing for 10 days to 14 days. The activity of an antibody in a culturing solution is investigated by ELISA and, regarding a cell of a well producing an objective antibody, a hybridoma is cloned by a limiting dilution method. By cloning, a stable hybridoma strain producing an anti-BSH antibody is obtained.

In the present invention, a hybridoma was made by the aforementioned method, and a plurality of hybridoma strains such as BSF-2 etc. were established. Among them, BSF-2 was deposited at International Patent Organism Depositary, National Institute of Advanced Industrial Science and Technology (postal code 305-8566, Ibaragi-ken, Tsukuba-shi, Higashi 1-1-1) on Oct. 2, 2006 under accession number ABP-10689. Also, BSF-2 was deposited domestically at National Institute of Advanced Industrial Science (postal code 305-8566, Ibaragi-ken, Tsukuba-shi, Higashi 1-1-1) on Feb. 22, 2006 under accession number FERM AP-20805.

The hybridoma of the present invention is cultured using a medium (e.g. DMEM containing 10% bovine fetal serum), and a supernatant from centrifugation of the culturing solution can be used as a monoclonal antibody solution. Alternatively, by injecting the present hybridoma into an abdominal cavity of an animal from which the hybridoma is derived, ascites is produced, and the resulting ascites can be used as a monoclonal antibody solution. These antibody solutions can be further purified and concentrated as described above.

Also, the present invention relates to a kit for measuring BSH, containing the antibody. The measuring kit of the present invention contains an antibody specifically binding to BSH, thereby, can simply measure BSH, and can be suitably used in a method of measuring BSH described later. The kit further contains a labeled secondary antibody or a labeled BSH hapten (antigen), a buffer, a detecting reagent and/or a BSH standard solution depending on a measuring method.

A preferable kit is a kit which can be used in an indirect competitive ELISA method or a direct competitive ELISA method shown below. When used in the direct competitive ELISA method, it is preferable that the present kit further contains a carrier to which the monoclonal antibody of the present invention is solid-phased. In this case, a step (1) of the direct competitive ELISA method described below can be omitted.

When used in the indirect competitive ELISA method, it is preferable that the present kit further contains a solid-phased antigen, and it is preferable that the kit contains a carrier to which the solid-phased antigen is solid-phased. In this case, a step (1) of the indirect competitive ELISA method described below can be omitted.

The solid-phased antigen contains a different hapten from a hapten used in preparing the antibody of the present invention. It is preferable that a hapten part of the solid-phased antigen is BSH-hexanoic acid.

In addition, the solid-phased antigen can be obtained by forming a complex of a hapten for the solid-phased antigen and a high-molecular compound (protein) such as bovine serum albumin (BSA), rabbit serum albumin (RSA), ovalbumin (OVA), Keyhole Limpet hemocyanin (KLH), thyroglobulin (TG), immunoglobulin and the like.

The hapten for the solid-phased antigen can be synthesized by the known method, or a commercially available product may be utilized. A method of forming a complex is not particularly limited, but can be performed by the known method. For example, a complex can be formed by reacting a carboxyl group of a hapten for the solid-phased antigen and a functional group (e.g. amino group) of the high-molecular compound by a mixed acid anhydride method or an active ester method.

The kit of the present invention, when used in the indirect competitive ELISA method described below, contains the solid-phased antigen, a carrier retaining a solid-phased antigen, a BSH antibody, a secondary antibody labeled with an enzyme, and a detecting reagent.

Further, the present invention relates to a method of measuring BSH, including using the antibody or the kit. A measuring method is not particularly limited as far as it is a usual method utilizing an antigen-antibody reaction, and includes a radioactive isotope element immunological measuring method (RIA), enzyme immunoassay (ELISA), a fluorescent or light emission measuring method, an aggregation method, an immunoblotting method, an immunochromatography method and the like (Meth. Enzymol., 92, 147-523 (1983), Antibodies Vol. II IRL Press Oxford (1989)). From a viewpoint of sensitivity and simplicity, ELISA is preferable. Examples of an enzyme used in ELISA include peroxidase, alkaline phosphatase, β-galactosidase, luciferase and the like.

Examples of the measuring method by ELISA include indirect competitive ELISA and direct competitive ELISA. For example, indirect competitive ELISA can be performed by the following procedure.

(1) A solid-phased antigen is solid-phased to a carrier.

A carrier used is not particularly limited as far as it is a carrier used in usual ELISA, but a microtiter plate of 96-well, 48-well, 192-well etc. is preferable. Solid-phasing may be performed, for example, by placing a buffer containing an antigen for solid-phasing on a carrier, followed by incubation. A concentration of an antigen in a buffer is usually around 0.01 to 100 μg/ml. As the buffer, the known buffer can be used depending on a detection means.

(2) In order to prevent non-specific adsorption of a protein onto a solid phase surface of a carrier, a solid phase surface part onto which an antigen for solid-phasing is not adsorbed is blocked with a protein having no relationship with an antigen.

As a blocking agent, BSA or a skim milk solution, or commercially available block Ace (manufactured by Dainippon Pharmaceutical Co., Ltd.) can be used. Blocking can be performed by adding the blocking agent to a carrier, incubating this, for example, at about 4° C. overnight, and washing this with a washing solution. The washing solution is not particularly limited, but the same buffer as that of the (1) can be used.

(3) A sample containing BSH at various concentrations and a solution of the monoclonal antibody of the present invention are added to a solid phase surface treated in the (1) and the (2), and the antibody is competitively reacted with the solid-phased antigen and BSH to produce a solid-phased antigen-antibody complex and a BSH-antibody complex.

The reaction can be usually performed at 4 to 37° C. for about 1 to 2 hours.

(4) By measuring an amount of the solid-phased antigen-antibody complex, an amount of BSH in a sample can be determined from a pre-produced calibration line.

An amount of the solid-phased antigen-antibody complex can be measured by adding a secondary antibody (antibody recognizing BSH antibody) labeled with an enzyme. For example, when a mouse monoclonal antibody is used as a BSH antibody, it is desirable that an anti-mouse-gout antibody labeled with an enzyme (e.g. peroxidase or alkaline phosphatase etc.) is used to react with a BSH antibody bound to a carrier. The reaction may be performed under the same condition as that of the (3). After the reaction, the reaction product is washed with a buffer.

(5) A chromogenic substrate solution reacting with an enzyme labeling a secondary antibody bound to a carrier is added, and an absorbance is measured, thereby, an amount of BSH can be calculated from a calibration line.

When peroxidase is used as an enzyme binding to a secondary antibody, for example, a chromogenic substrate solution containing hydrogen peroxide, and 3,3',5,5'-tetramethylbenzidine or o-phenylenediamine can be used. Usually, after a chromogenic substrate solution is added to react at room temperature for about 10 minutes, sulfuric acid is added to stop an enzymatic reaction. When 3,3',5,5'-tetramethylbenzidine is used, an absorbance at 450 nm is measured. When o-phenylenediamine is used, an absorbance at 490 nm is measured. In addition, in order to correct a background value, it is desirable to measure an absorbance at 630 nm, simultaneously.

When alkaline phosphatase is used as an enzyme binding to a secondary antibody, for example, there is a method of developing a color using p-nitrophenylphosphoric acid as a substrate, adding a NaOH solution to stop an enzymatic reaction, and measuring an absorbance at 415 nm.

A decrease rate of an absorbance of a solution which was reacted with an antibody by addition of BSH relative to an absorbance of a reaction solution with no BSH added is calculated as an inhibition rate. Using a calibration line which was pre-produced by an inhibition rate of a reaction solution with BSH of the known concentration added, a concentration of BSH in a sample can be calculated.

As another aspect, measurement of BSH can be also performed, for example, by direct competitive ELISA using the monoclonal antibody of the present invention described below.

(1) The monoclonal antibody of the present invention is solid-phased to a carrier.

As a carrier used, a microtiter plate of 96-well, 48-well, 192-well etc. is preferable. Solid-phasing may be performed, for example, by placing a buffer containing an antibody for solid-phasing on a carrier, followed by incubation. A concentration of an antibody in a buffer is usually around 0.01 to 100 μg/ml. As the buffer, the known buffer can be used depending on a detection means.

(2) In order to prevent non-specific adsorption of a protein onto a solid phase surface of a carrier, a solid phase surface part onto which an antibody for solid-phasing is not adsorbed is blocked with a protein having no relationship with an antibody.

As a blocking agent, BSA or a skim milk solution, or commercially available Block Ace (manufactured by Dainippon Pharmaceutical Co., Ltd.) can be used. Blocking is performed by adding the blocking agent to a carrier, incubating this, for example, at about 4° C. overnight, and washing this with a washing solution. The washing solution is not particularly limited, but the same buffer as that of the (1) can be used.

(3) A mixture in which an enzyme-bound hapten obtained by binding a BSH hapten and an enzyme is added to a sample containing BSH having various concentrations is prepared.

Preparation of an Enzyme-Bound Hapten May be Performed by any method as far as it is a method of binding a BSH hapten to an enzyme, being not limiting.

(4) The mixture of a step (3) is reacted with the antibody solid-phased carrier obtained in a step (2).

By a competitive inhibitory reaction of BSH and an enzyme-bound hapten, a complex of these and a solid-phased carrier is produced. The reaction is performed, for example, at about 25° C. for about 1 hour. After completion of the reaction, the carrier is washed with a buffer, to remove an enzyme-bound hapten which has not been bound to a solid-phased antibody.

By measuring an amount of a solid-phased antibody-enzyme-bound hapten complex, an amount of BSH in a sample is determined from a pre-produced calibration line.

By adding a chromogenic substrate solution reacting with an enzyme of an enzyme-bound hapten in the present step as in the aforementioned indirect competitive inhibition ELISA method, and measuring an absorbance, an amount of BSH can be calculated from a calibration line.

In the measuring method of the present invention, pretreatment is performed depending on a subject to be measured to obtain a sample, and the sample is subjected to a step (3) of the indirect competitive ELISA or the direct competitive ELISA.

Using a monoclonal antibody produced from hybridoma BSF-2 of the present invention, a method of measuring BSH can be performed. By using the present antibody, specific and highly sensitive measurement of BSH which has not previously been measured by immunoassay can be performed.

As another aspect of the present invention, using the monoclonal antibody of the present invention in an immunological staining method, behavior in a living body of BSH accompanied with BNCT, particularly, a microdistribution of a cell superficial layer or a cell can be investigated.

In addition, the hybridoma of the present invention can stably produce the monoclonal antibody in a short term and, by culturing the hybridoma, a monoclonal antibody which molecular-recognizes BSH with high sensitivity can be produced.

EXAMPLES

The present invention will be specifically explained below by way of Examples. A person skilled in the art can easily modify or alter the present invention based on the description of the present description, and they are included in the technical scope of the present invention.

In the following Examples, analysis, separation and purification of a compound were performed using the following equipments and reagents.

NMR spectrum: JMTC-400/54/SS 400 MHz (manufactured by JEOL. Ltd.)

Unless otherwise indicated, TMS was used as an internal standard. In addition, a chemical shift described below was shown by a δ value.

Silica gel for column chromatography: BW-200 (manufactured by Fuji Silysia Chemical Ltd.)

Example 1

Synthesis of BSH Hapten (a) Synthesis of BSH-Hexanoic Acid Ethyl Ester (3)

BSH (101 mg, 0.46 mmol) was dissolved in acetonitrile (10 mL), bromohexanoic acid ethyl ester (0.2 mL, 1.12 mmol) was slowly added dropwise while stirring at room temperature, and the mixture was stirred at room temperature for 2 days. Thereafter, acetonitrile was removed by concentration under reduced pressure, and the concentration residue was purified by silica gel column chromatography (chloroform:methanol=9:1) to obtain a yellow oil (101 mg, yield 67.4%).

TLC: Rf=0.58 (chloroform:methanol=3:1)

$^1$H-NMR (DMSO) δ (ppm): 0.60-2.10 (m), 1.08 (t, 3H, J=7.08 Hz), 1.34-1.42 (m, 2H), 1.52-1.59 (m, 2H), 1.63-1.70 (m, 2H), 2.19 (t, 2H, J=7.32 Hz), 2.77 (m, 2H), 3.95 (q, 2H, J=7.08 Hz)

(b) Synthesis of BSH-Hexanoic Acid (4)

A compound (113.7 mg, 0.31 mmol) obtained in the (a) was dissolved in methanol (2.0 mL), 2N sodium hydroxide (0.63 mL) was added dropwise, and the mixture was stirred at room temperature for 6 hours. The reaction solution was washed using ethyl acetate, 1N hydrochloric acid was added to a pH of 3, and the resultant was extracted with ethyl acetate. Thereafter, the extract was washed with water and an aqueous saturated sodium chloride solution, dried with magnesium sulfate, and concentrated under reduced pressure to remove ethyl acetate, and the concentration residue was purified by silica gel column chromatography (chloroform:methanol=4: 1) to obtain a yellow oil (69.9 mg, yield 67.4%).

TLC:Rf=0.30 (chloroform:methanol=2:1)

$^1$H-NMR (DMSO) δ (ppm): 0.60-2.10 (m), 1.30-1.37 (m, 2H), 1.45-1.53 (m, 2H), 1.63-1.73 (m, 2H), 2.20 (t, 2H, J=7.32 Hz), 2.85 (m, 2H)

Example 2

Preparation of Immunogen (c) Synthesis of BSH-Hexanoic Acid-BSA Complex (Immunogen Using BSA)

Bovine serum albumin (11 mg, 164 mmol) and 760 μL of a borate buffer (sodium tetraborate 50 mmol, sodium chloride 15.4 mmol, sodium azide 0.3 mmol/pure water 100 mL) having a pH of 9.4 were added to a Saint tube, the mixture was stirred at 4° C. overnight, and DMF (40 μL) was added (I solution).

The compound (6.0 mg, 18 μmol) obtained in the (b), N-hydroxysuccinic acid imide (1.5 mg, 13.3 μmol), 1-ethyl-3-(3-dimethylaminopropyl)-carbodiimide hydrochloride (2.5 mg, 13.3 μmol) and DMF (200 μL) were added to another Saint tube, and the mixture was stirred at room temperature overnight (II solution).

The II solution was added dropwise to the I solution (10 μL/5 minutes), and the mixture was stirred at room temperature for 2.5 hours, and stirred at 4° C. overnight. The mixture was dialyzed with a 10% isopropanol-phosphoric acid buffer for about 60 hours (a buffer was exchanged six times) to obtain a BSH-hexanoic acid-BSA complex (bound body). A boron concentration of the complex was measured by ICP analysis, and it was transferred to a 1.5 mL Eppentube, and stored at 4° C.

(d) Synthesis of BSH-Hexanoic Acid-KLH Complex (Immunogen Using KLH)

As an immunogen, a bound body of KLH and the BSH hapten of the present invention were prepared as in the (c).

Example 3

Production of Polyclonal Antibody

The BSH hapten-KLH bound body prepared in Example 2 was diluted with a phosphate buffer (pH 7.4) to 1 mg/mL. 600 μL of this antigen solution was mixed with a RIBI adjuvant (MPL+TDM Adjuvant System, SIGMA M6536), and sufficiently mixed by vortexing for 2 to 3 minutes. It was intraperitoneally injected into five Balb/c mice (8 week old, male) to immunize them (50 μg/dose). The injection was performed every two weeks and, after third immunization, blood was taken one week after each immunization (orbit blood collection).

The antigen (BSH hapten-BSA bound body) prepared in Example 2 was diluted with PBS (pH 7.4) to 5.0 μg/mL, each 100 μL was dispensed into a microplate for ELISA, and it was allowed to stand at 37° C. for 1 hour to fix the antigen on a plate surface.

Thereafter, the plate was washed with a PBS-Tween solution (Phosphate buffer, pH 7.4, 0.05% Tween 20), each 200 μL of a blocking solution (phosphate buffer, pH 7.4, 1% Block Ace) was added in order to prevent non-specific adsorption, and it was allowed to stand at 37° C. for 1 hour to perform blocking, and it was washed with a PBS-Tween solution, 100 μL of the prepared sample was added, and it was allowed to stand again at 37° C. for 1 hour. After washing with a PBS-Tween solution, 50 μL of a secondary antibody was added, and it was allowed to stand at 37° C. for 1 hour to react with a secondary antibody (HRP-raveled gout anti-mouse IgG (γ chain specific)).

It was washed with a PBS-Tween solution, 200 μL of an already prepared substrate solution (phosphate citrate buffer (pH 5.0), 0.04% o-phenylenediamine) which had been adjusted to 0.02% aqueous hydrogen peroxide, was added. It was allowed to stand at 37° C. for 30 minutes to develop a color, and an absorbance was measured using a microplate reader (BIO-RAD/Model550).

Example 4

Production of Hybridoma and Monoclonal Antibody (a) Immunization of Animal and Preparation of Antibody-Producing Cell The synthesized BSH hapten-KLH bound body (Example 2) was diluted with a phosphate buffer, pH 7.4 (PBS) (NaCl 137 mM, NaHPO$_4$.12H$_2$O 8.10 mM, KCl 2.68 mM, KH$_2$PO$_4$ 1.47 mM) to 500 μg/mL. 2 mL of this antigen solution was mixed with a RIBI adjuvant system (RIBI/MPL (registered trade mark)+TDM Emulsion, R-700) which had been warmed to 40° C. for 10 minutes, and this was vortexed for 2 to 3 minutes to mix well.

The mixture was subcutaneously injected into five Balb/c mice (8 week old, male) to immunize them (50 μg/dose). The injection was performed every two weeks and, after second immunization, blood was taken (orbit blood collection) after one week from each immunization. Taken blood was collected in a 1.5 mL tube, incubated at 37° C. for 1 hour, and allowed to stand at 4° C. overnight.

(b) Cell Fusion (b-1) Preparation of DMEM Medium

MilliQ was added to one pack of a Dulbecco's modified Eagle medium (IWAKI DME/LOW, Lot.99562013), 78.4 mg of gentamycin sulfate (gentamycin 642 μg/mg, SIGMA Lot.105H0457), and 2.2 g of sodium bicarbonate (Kanto Kagaku, Lot.302F1378) to 1 L, and the mixture was sterilized with a 0.22 μm filter (MILLIPORE MILLEX (registered trade mark)-GV, 0.22 μm filter SLGV01352) to prepare a DMEM medium.

(b-2) Preparation of HAT Medium and HT Medium 10 mL of sterilized MilliQ was added to one bottle of HAT supplement (SIGMA, Lot#61K8934) to completely dissolve a reagent in the bottle. This solution was added at an amount which is 1/50 an amount of a DMEM medium (15% FCS), and was mixed to obtain a HAT medium. 10 mL of sterilized MilliQ was added to one bottle of HT supplement (SIGMA, Lot#32K8928) to completely dissolve a reagent in the bottle, and this solution was added at an amount which is 1/50 an amount of a BMEM medium (15% FCS), and was mixed to obtain a HT medium.

(b-3) Preparation of 50% PEG Medium 20 g of PEG6000 (PEG#6000 (M.W.7300-9000), Nakaraitesk, Lot M8H2950) was added to 20 mL of a DMEM medium, and the mixture was stirred with a hot stirrer for 2 hours to completely dissolve it. Thereafter, the mixture was measured up to 40 mL, and sterilized using a 0.20 µm filter in a clean bench. Thereafter, each 1.8 mL was dispensed, frozen, and thawed immediately before use, and 200 µL of DMSO (SIGMA, Lot#42K2401) was added to prepare a 50% PEG (10% DMSO) solution.

(b-4) Preparation of ACK Lysis Buffer 802.3 mg of ammonium chloride, 10.01 mg of potassium bicarbonate, and 3.72 mg of EDTA were added to 90 mL of MilliQ to adjust a pH to 7.2-7.4, and this was measured up to 100 mL. This was placed into a medium bottle, autoclaved at 121° C. for 20 minutes to sterilize it, thereby, an ACK lysis buffer (0.15M ammonium chloride, 1.0 mM potassium bicarbonate, 0.1 mM EDTA, pH 7.2-7.4) was obtained.

(c) Preparation of Spleen Cell

A mouse, an antibody value of which had reached saturation, was finally immunized (tale vein injection) and, after three days, a spleen was isolated. The isolated spleen was placed into a Petri dish containing DMEM on an ice, and this as placed in a clean bench. Unnecessary parts of the isolated spleen were removed, and the resultant was placed into a 5 mL Petri dish containing a fresh DMEM medium. Using two tweezers, spleen cells were scraped out, and filtered with a cell strainer (FALCO-N2350, 70 µm nylon) to remove unnecessary materials, and passed cells were collected in a glass centrifugation tube, which was centrifuged at 1000 rpm for 10 minutes.

A supernatant was discarded, 5 mL of an ACK lysis buffer was added, and the mixture was uniformly mixed by pipetting, allowed to stand at room temperature for 5 minutes, and washed to remove spleen cells (removal of erythrocyte). 20 mL of a DMEM medium was added thereto, and the mixture was centrifuged at 1000 rpm for 10 minutes to remove a supernatant. Further, 20 mL of a DMEM medium was added, and cells were washed by pipetting, and centrifuged at 1000 rpm for 10 minutes. A supernatant was removed, 10 mL of a DMEM medium was added and was mixed by pipetting, and the number of cells was counted using a hemocyte calculating disk (Erma Tokyo4062).

(d) Preparation of Myeloma Cell

A myeloma cell (P3X63Ag8U.1) was cultured bringing into line with schedule for cell fusion and, immediately before use, cells were collected in a glass centrifuge tube, which was centrifuged at 1000 rpm for 10 minutes. A supernatant was removed, 10 mL of a DMEM medium was added, this was mixed by pipetting, and the number of cells was counted using a hemocyte calculating disk (Erma Tokyo4062).

(e) Cell Fusion

An amount of a myeloma cell suspension was adjusted so that spleen cell:myeloma cell became 10:3, and this was placed into a centrifuge tube for a spleen cell suspension, and mixed by pipetting. This was centrifuged at 1000 rpm for 10 minutes to remove a supernatant, and a supernatant was completely removed using a Pasteur pipette.

Thereafter, a centrifuge tube was tapped to spread cells on a wall of the centrifuge tube. The centrifuge tube was warmed with a hand, and 1 mL of a 50% PEG (10% DMSO) solution was gradually added over 1 minute while rotating. The centrifuge tube was rotated while warming for 1 minute, 2 mL of a DMEM medium was added over 2 minutes, and 8 mL of a DMEM medium was further added over 5 minutes by the similar method.

Thereafter, this was centrifuged at 1000 rpm for 10 minutes, a supernatant was discarded, 10 mL of a DMEM medium was further added to wash cells, which was centrifuged at 1000 rpm for 10 minutes. A supernatant was removed, a DMEM (15% FCS) medium was adjusted to a cell density of $2 \times 10^5$ cells/mL, and each 100 µL was dispensed into a 96-well plate, and allowed to stand at 37° C. overnight.

(f) HAT Collection

Each 100 µL which was about 2-fold of a HAT medium was dispensed to cells which had been dispensed into a 96-well plate, and this was allowed to stand at 37° C. for one week. Thereafter, 100 µL of a HAT medium was added. Thereafter, hybridoma cells of a positive well were transferred to a 24-well plate, and a HT medium was used to adjust a total amount to 1 mL. Three days after, secondary screening was performed, and a positive well was cloned by a limiting dilution method.

(g) Cloning Using Limiting Dilution Method

The number of hybridoma cells of a well which had been positive by secondary screening was counted using a hemocyte calculating disk (Erma Tokyo4062) to obtain a concentration, and stepwise dilution was performed using a medium for cloning (DMEM (15% FCS) medium 20 mL, Briclone 1 mL), to adjust to 10 cells/mL and 5 cells/mL. Each 100 µL was dispensed into a 96-well plate so that the number of cells was 1 or 0.5 per well.

This was allowed to stand at 37° C. for 1 week, thereafter, each 100 µL of a cloning-positive medium was added to each well, and this was further allowed to stand at 37° C. for 1 week. Cells which had been positive were transferred to a 48-well plate, second cloning was performed similarly, and finally, a single hybridoma cell was obtained.

(h) Purification of Antibody from Serum-Free Medium

The culturing solution of hybridoma cell BSF-2 which had been cultured in a serum-free medium was centrifuged at 1000 rpm for 10 minutes, and ammonium sulfate was added to a cell supernatant to an ammonium sulfate concentration of 60%, to precipitate an antibody protein. This was stirred at 4° C. for 2 hours, and further allowed to stand overnight. Thereafter, this was centrifuged at 4° C. and 13500 rpm for 20 minutes, dissolved in a binding buffer, and dialyzed with a binding buffer.

After dialysis, this was centrifuged at 8000 rpm for 10 minutes, and a supernatant was filtered with a 0.45 µm filter to obtain a sample. 5 mL of ultrapure water was pumped to a column at a flow rate of one droplet/sec (1-2 mL/minute), 3 to 5 mL of a binding buffer was pumped at a flow rate of one droplet/sec (1-2 mL/minute) to equilibrate a column. Thereafter, a prepared sample was pumped at one droplet/2 seconds (1-2 mL/minute) to adsorb an antibody onto a column.

Non-adsorbed components were removed by pumping 3 to 5 mL of a binding buffer (20 mM sodium phosphate, 0.8M ammonium sulfate, pH 7.5) at a flow rate of one droplet/sec, and 5 mL of an eluting buffer (20 mM sodium phosphate, pH 7.5) was pumped at one droplet/sec (1-2 mL/minute) to elute an antibody. Each 0.5 mL of an eluant was recovered.

An absorbance (OD=280 nm) of all fractions was measured, and an antibody protein concentration of fractions containing an antibody protein was measured by a Bloodford method. Thereafter, purity of a monoclonal antibody was confirmed by SDS-PAGE. In addition, a nucleotide sequence and an amino acid sequence of the resulting monoclonal antibody are shown in FIGS. 2 to 4.

(i) Measurement of Sensitivity of Antibody and Production of Calibration Line (Direct Competitive ELISA Method)

Using a PBS solution (phosphate buffer pH 7.4), each 100 μL of a monoclonal antibody (prepared from hybridoma strain BSF-2) solution which had been adjusted to 5 μg/mL was dispensed into a 96-well ELISA plate, and this was allowed to stand at 37° C. for 1 hour to solid-phase an antibody on a plate. After the reaction, this was washed with a PBS-Tween solution (phosphatebuffer (pH 7.4), 0.05% Tween20), a blocking solution (phosphate buffer) (pH 7.4), 1% BSA) was added to a plate in order to prevent non-specific adsorption, and this was reacted at room temperature for 1 hour or at 4° C. overnight, to perform blocking.

After washing with a PBS-Tween solution, a sample was prepared so that a concentration of BSH was 100 to 0.001 ppm, respectively, in a PBS solution (0.5 μg/mL) of a HRP-labeled competing agent (HRP-bound BSH-hexanoic acid).

Each 100 μL of the prepared sample was added to a 96-well ELISA plate (IWAKI 3801-096) to react at 37° C. for 1 hour. Thereafter, ELISA (base solution (50 mmol phosphate citrate buffer (pH 5.0), 0.04% o-phenylenediamine) was performed according to a conventional method, and an absorbance at 490 nm was measured using a microplate reader (BIO-RAD/Model1550).

Results of measurement are shown in FIG. 1. An axis indicates a BSA concentration, and a Y axis indicates an absorbance. As shown by FIG. 1, BSH can be specifically detected using a monoclonal antibody prepared from hybridoma strain BSF-2, and it was possible to measure a concentration of BSH by absorbance measurement in a wide range of a BSH concentration of 0.001 to 1 μM. Like this, by using the hybridoma and the antibody of the present invention, quantitative assessment and qualitative assessment with a very high sensitivity in a wide concentration range of BSH become possible.

The invention claimed is:

1. A hybridoma producing a monoclonal antibody, wherein the hybridoma is BSF-2 (accession number FERM BP-10689).

2. A monoclonal antibody produced by the hybridoma BSF-2 (accession number FERM BP-I0689).

3. A monoclonal antibody to mercaptoundecahydrododecaborate (BSH), wherein the heavy chain of the antibody has at least 90% homology to SEQ ID NO:3 and the light chain of the antibody has at least 90% homology to SEQ ID NO:4.

4. A kit for measuring mercaptoundecahydrodecaborate (BSH), comprising a monoclonal antibody as defined in claim 3.

* * * * *

```
                        SEQUENCE LISTING

<160> NUMBER OF SEQ ID NOS: 4

<210> SEQ ID NO 1
<211> LENGTH: 657
<212> TYPE: DNA
<213> ORGANISM: mouse

<400> SEQUENCE: 1
ctcgagtctg gccctggaat attgcagcgc tcccagaccc tcagtctgac ttgttctttc      60
tctgggtttt cactgagcac ttctggtatg ggtgttggct ggtttcgtca gccttcaaca     120
aagggtctag agtggctggc agacatttgg tggaatgaca ataaatacta taatccatcc     180
ctgaagagcc ggctcacaat ctccaaggat acctccaaaa accaggtatt cctcaagatc     240
gccagtgtgg acactataga tactgccact tactactgtt ctctaagaaa tagtgccgaa     300
aagacaaaca cctggggcca aggcaccact ctcacagtct cctcagccaa aacgacaccc     360
ccatctgtct atccactggc ccctggatct gctgcccaaa ctaactccat ggtgaccctg     420
ggatgcctgg tcaagggcta tttccctgag ccagtgacag tgacctggaa ctctggatcc     480
ctgtccagcg gtgtgcacac cttcccagct gtcctgcagt ctgacctcta cactctgagc     540
agctcagtga ctgtcccctc cagcacctgg cccagcgaga ccgtcacctg caacgttgcc     600
cacccggcca gcagcaccaa ggtggacaag aaaattgtgc cagggattg tactagt        657

<210> SEQ ID NO 2
<211> LENGTH: 655
<212> TYPE: DNA
<213> ORGANISM: mouse

<400> SEQUENCE: 2
gagctcgttg tgactcagga atctgcactc accacatcac ctggtgaaac agtcacactc      60
acttgtcgct caagtactgg ggctgttaca actagtaact atgtcaattg ggtccaagaa     120
aaaccagatc atttattcac tggtctaata ggtggtacca caaccgagc tccaggtgtt     180 cctgccagat tctcaggctc cctgattgga gacaaggctg ccctcaccat cacagggca     240 cagactgagg atgaggcaat atatttctgt ggtctatggt acagcaacca ttgggtgttc     300
ggtggaggaa ccaaactgac tgtcctaggc cagcccaagt cttcgccatc agtcaccctg     360
tttccacctt cctctgaaga gctcgagact aacaaggcca cactggtgtg tacgatcact     420
gatttctacc caggtgtggt gacagtggac tggaaggtag atggtacccc tgtcactcag     480
```

-continued

```
ggtatggaga caacccagcc ttccaaacag agcaacaaca agtacatggc tagcagctac      540
ctgaccctga cagcaagagc atgggaaagg catagcagtt acagctgcca ggtcactcat      600
gaaggtcaca ctgtggagaa gagtttgtcc cgtgctgagt gttcctaatt ctaga           655
```

<210> SEQ ID NO 3
<211> LENGTH: 219
<212> TYPE: PRT
<213> ORGANISM: mouse

<400> SEQUENCE: 3

```
Leu Glu Ser Gly Pro Gly Ile Leu Gln Arg Ser Gln Thr Leu Ser Leu
1               5                   10                  15

Thr Cys Ser Phe Ser Gly Phe Ser Leu Ser Thr Ser Gly Met Gly Val
            20                  25                  30

Gly Trp Phe Arg Gln Pro Ser Thr Lys Gly Leu Glu Trp Leu Ala Asp
        35                  40                  45

Ile Trp Trp Asn Asp Asn Lys Tyr Tyr Asn Pro Ser Leu Lys Ser Arg
    50                  55                  60

Leu Thr Ile Ser Lys Asp Thr Ser Lys Asn Gln Val Phe Leu Lys Ile
65                  70                  75                  80

Ala Ser Val Asp Thr Ile Asp Thr Ala Thr Tyr Tyr Cys Ser Leu Arg
                85                  90                  95

Asn Ser Ala Glu Lys Thr Asn Thr Trp Gly Gln Gly Thr Thr Leu Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
    130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190

Glu Thr Val Thr Cys Asn Val Ala His Pro Ala Ser Ser Thr Lys Val
        195                 200                 205

Asp Lys Lys Ile Val Pro Arg Asp Cys Thr Ser
    210                 215
```

<210> SEQ ID NO 4
<211> LENGTH: 215
<212> TYPE: PRT
<213> ORGANISM: mouse

<400> SEQUENCE: 4

```
Glu Leu Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Val Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80
```

```
Gln Thr Glu Asp Glu Ala Ile Tyr Phe Cys Gly Leu Trp Tyr Ser Asn
                85                  90                  95

His Trp Val Phe Gly Gly Gly Thr Lys Leu Thr Val Leu Gly Gln Pro
            100                 105                 110

Lys Ser Ser Pro Ser Val Thr Leu Phe Pro Pro Ser Ser Glu Glu Leu
        115                 120                 125

Glu Thr Asn Lys Ala Thr Leu Val Cys Thr Ile Thr Asp Phe Tyr Pro
    130                 135                 140

Gly Val Val Thr Val Asp Trp Lys Val Asp Gly Thr Pro Val Thr Gln
145                 150                 155                 160

Gly Met Glu Thr Thr Gln Pro Ser Lys Gln Ser Asn Asn Lys Tyr Met
            165                 170                 175

Ala Ser Ser Tyr Leu Thr Leu Thr Ala Arg Ala Trp Glu Arg His Ser
            180                 185                 190

Ser Tyr Ser Cys Gln Val Thr His Glu Gly His Thr Val Glu Lys Ser
        195                 200                 205

Leu Ser Arg Ala Glu Cys Ser
    210                 215
```